_United States Patent_ [19]

Ohashi et al.

[11] 4,325,886

[45] Apr. 20, 1982

[54] OPTICAL RESOLUTION OF ACYLTHIOPROPIONIC ACID

[75] Inventors: Naohito Ohashi, Nishinomiya; Hiroyuki Mizote, Ibaraki; Isamu Maruyama, Minoo; Shoji Nagata, Toyonaka; Kikuo Ishizumi, Toyonaka; Junki Katsube, Toyonaka, all of Japan

[73] Assignee: Sumitomo Chemical Company, Limited, Osaka, Japan

[21] Appl. No.: 209,680

[22] Filed: Nov. 24, 1980

[30] Foreign Application Priority Data

Dec. 7, 1979 [JP] Japan ................. 54-159456

[51] Int. Cl.$^3$ .................. C07C 153/07; C07C 153/09
[52] U.S. Cl. ........................... 260/455 R; 562/401; 260/326.84
[58] Field of Search ............. 260/455 R; 562/401

[56] References Cited

U.S. PATENT DOCUMENTS 4,224,457  9/1980  Iwao et al. ................ 260/455 R X _Primary Examiner_—Natalie Trousof
_Assistant Examiner_—Vera C. Clarke
_Attorney, Agent, or Firm_—Stevens, Davis, Miller & Mosher

[57] ABSTRACT

A process for the optical resolution of DL-α-methyl-β-acylthiopropionic acid, which comprises contacting a DL-α-methyl-β-acylthiopropionic acid of the formula,

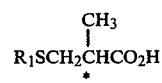

wherein $R_1$ is acetyl or benzoyl which may be substituted with a $C_1$-$C_3$ alkyl or a halogen atom, with an optically active amine of the formula,

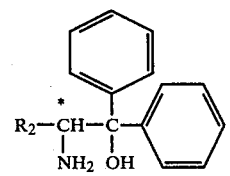

wherein $R_2$ is methyl, isopropyl or isobutyl, to form diastereoisomeric salts, subjecting the formed diastereoisomeric salts to the fractional crystallization in a solvent to separate the D-acid salt from the L-acid salt, and then contacting the individual diastereoisomeric salt with acid to give D-α-methyl-β-acylthiopropionic acid and L-α-methyl-β-acylthiopropionic acid, the former being useful as an intermediate for synthesizing captopril useful as an antihypertensive agent.

6 Claims, No Drawings

OPTICAL RESOLUTION OF ACYLTHIOPROPIONIC ACID

The present invention relates to a process for the optical resolution of racemic carboxylic acids.

More particularly, this invention relates to a process for the optical resolution of DL-α-methyl-β-acylthiopropionic acid of the formula [I],

wherein $R_1$ is acetyl or benzoyl which may be substituted with a $C_1$-$C_3$ alkyl or a halogen atom.

As defined above, the term $C_1$-$C_3$ alkyl means straight or branched chain alkyl group having from 1 to 3 carbon atoms (e.g. methyl, ethyl, propyl), and the term "halogen" includes fluorine, chlorine, bromine and iodine.

The optically active α-methyl-β-acylthiopropionic acids resolved according to the process of the present invention are useful as intermediate for the production of medicines (e.g., captopril or its congeners).

Captopril, N-(D-α-methyl-β-mercaptopropionyl)-L-proline [II],

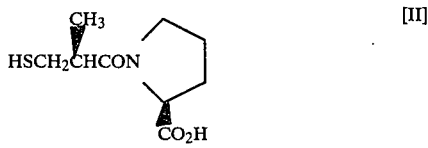

is now known to be useful as antihypertensive agent. It inhibits angiotensin converting enzyme and possesses remarkable antihypertensive activity. [Biochemistry, 16, 5487 (1977)].

A typical synthesis method of the compound of the formula [II] is disclosed in U.S. Pat. No. 4,046,889.

An amidation reaction between DL-α-methyl-β-acylthiopropionic acid [I] and L-proline gives a mixture of two kinds of diastereoisomer having the formulas [II'] and [II''],

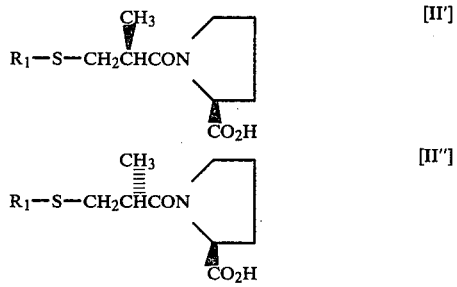

wherein $R_1$ is as defined above.

After isolating the D-type propionyl compound of the formula [II'], the acyl group represented by $R_1$ is removed to obtain the objective compound [II].

It is considered that the above method has a drawback in forming an almost equal amount of L-type propionyl compound of the formula [II''] as a by-product, and the expensiveness of the L-proline as a starting material amplifies such drawback. Under such circumstances, the present inventors have found the fact that the drawback of forming the undesired diastereomer of the formula [II''] as a by-product can be avoided by employing a preliminarily resolved D-α-methyl-β-acylthiopropionic acid of the formula [I] in place of the DL-α-methyl-β-acylthiopropionic acid of the formula [I].

That is, it has been confirmed that the product obtained from the D-α-methyl-β-acylthiopropionic acid of the formula [I] as a starting material by converting to acid chloride derivative and then condensing with L-proline by applying the most economical condensation process of Schotten-Baumann type reaction, substantially gives only the objective compound of the formula [II'].

As the above result, it can be said that the process of the present invention provides an economically advantageous process for preparing N-(D-α-methyl-β-mercaptopropionyl)-L-proline (captopril) having the formula [II] which is a most useful antihypertensive agent.

Generally, the optical resolution of dl-carboxylic acids has been accomplished according to an ordinary fractional crystallization of diastereoisomeric salts consisting of optically active carboxylic acids and optically active amines such as quinidine, cinchonidine, brucine, ephedrine or α-methylbenzylamine.

In the case of DL-α-methyl-β-acylthiopropionic acids, however, it was difficult to carry out such optical resolution by using these conventional resolution reagents. For example, solubility difference between a D-acid-ephedrine salt and L-acid-ephedrine salt was so slight in various solvents that it was difficult to separate the diastereoisomeric salts from each other by fractional crystallization, and perservering fractional crystallization of the diastereoisomeric salts could separate the D-acid salt from the L-acid salt in only a low optical yield.

The present inventors further tried optical resolution of DL-α-methyl-β-acylthiopropionic acid by using optically active quinidine, α-methylbenzylamine and brucine. However, the fractional crystallization of the resulting diastereoisomers and the recovery of the said amines required complicated and troublesome treatment.

Upon such circumstances as mentioned above, the present inventors have found, unexpectedly, that optically active amines of the formula [III],

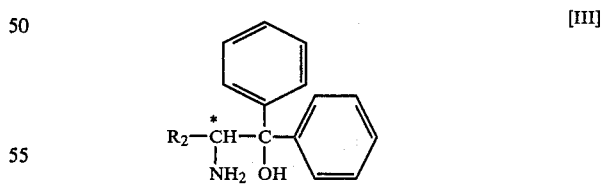

wherein $R_2$ is methyl, isopropyl or isobutyl, are very effective reagents for the optical resolution of DL-α-methyl-β-acylthiopropionic acid [I].

Thus the present invention provides a process for the optical resolution of DL-α-methyl-β-acylthiopropionic acid [I], which comprises contacting a DL-α-methyl-β-acylthiopropionic acid of the formula [I] with an optically active amine of the formula [III] to form diastereoisomeric salts, subjecting the formed diastereoisomeric salts to the fractional crystallization in a solvent to separate the D-acid salt from the L-acid salt, and then contacting the individual diastereoisomeric salt with an acid to give D-α-methyl-β-acylthiopropionic acid and L-α-methyl-β-acylthiopropionic acid.

The process of the present invention is disclosed in more detail below.

An equimolar or less amount of optically active (S- or R-) amino alcohol derivative [III] is added to DL-α-methyl-β-acylthiopropionic acid [I] in a solvent to prepare a solution containing diastereomer salts. The amount of the resolving reagent may vary, but is usually in the range of 0.5 to 1 mole to 1 mole of the racemic mixture to be resolved. When the optically active resolving reagent is used in an amount of less than 1 mole (e.g. 0.5 mole), the remaining amount (e.g. 0.5 mole) of an optically inactive amine or an inorganic base may be added.

The solvent used in the present invention is a neutral solvent. Acidic solvents (e.g. acetic acid) and basic solvents (e.g. amines) are excluded because they inhibit the formation of the diastereomer salts. In view of the easy operability and low cost, suitable examples of the solvent are water, ketones such as acetone, methyl ethyl ketone, alcohols having 1 to 4 carbon atoms such as methanol, ethanol, isopropanol, or aqueous mixture of these ketones or alcohols, or ethyl acetate, toluene, acetonitrile, or a mixture thereof. Preferred solvent is water, alcohols or an aqueous mixture thereof.

The resolution procedure is usually carried out at room temperature, but may be carried out at a higher or lower temperature. In order to obtain a uniform solution, the mixture may be heated up to the boiling point of the solvent, and the reaction mixture may optionally be cooled gradually in order to obtain a pure diastereomer salt.

By the resolution procedure, the diastereomer salt having less solubility is crystallized out from the reaction mixture. In case of using S-2-amino-1,1-diphenylpropanol as the resolving reagent of DL-α-methyl-β-acetylthiopropionic acid, the diastereomer salt having less solubility is a salt of D-α-methyl-β-acetylthiopropionic acid, and a salt of L-α-methyl-β-acetylthio-propionic acid remains in the solution. In case of using S-2-amino-1,1-diphenylpropanol as the resolving reagent of DL-α-methyl-β-benzoylthiopropionic acid the diastereomer salt having less solubility is a salt of L-α-methyl-β-benzoylthioprionic acid, and a salt of D-α-methyl-β-benzoylthiopropionic acid remains in the solution.

The diastereomer salt crystallized out from the reaction mixture is recrystallized from an alcohol or ketone solvent in order to improve the optical purity. The diastereomer salt remaining in the mixture can be isolated from the mixture by concentrating the filtrate obtained after removing the diastereomer salt firstly crystallized out and then collecting the resulting precipitates.

The diastereomer salts thus resolved can each be decomposed into the optically active (D- or L-) α-methyl-β-acylthiopropionic acid [I] by conventional methods. For example, the diastereomer salt firstly crystallized out or obtained from the filtrate is added to an aqueous solution of a mineral acid, such as hydrochloric acid, sulfuric acid, phosphoric acid, or the like, and thereby the desired optically active (D- or L-) α-methyl-β-acylthiopropionic acid [I] is obtained from the organic layer. The resolving reagent, optically active amino alcohol derivative [III] moves into the aqueous layer.

Further, the waste L-α-methyl-β-acylthiopropionic acid formed by the above optical resolution process may be converted again into the DL form by heating in the presence of a salt of an organic acid with a base.

The starting racemic α-methyl-β-acylthiopropionic acid can be prepared by the procedures as described in U.S. Pat. No. 4,046,889. The optically active amino alcohol derivatives [III] used as the resolving reagent is also known [cf. J. Chem. Soc., 287 (1925), 785 (1926); J. Pharm. Soc., Japan 48, 46 (1928)] and can easily be produced from an optically active α-amino acid by a single step as shown in the following reaction scheme A:

Reaction Scheme A

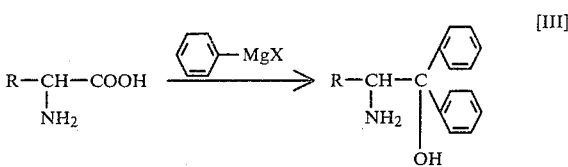

wherein R is as defined above, and X is a halogen atom.

The present invention is illustrated by the following Examples, but is not limited thereto.

EXAMPLE 1

DL-α-methyl-β-acetylthiopropionic acid (5.0 g) is mixed with water (60 ml) and heated to 50° C. To the mixture is added with stirring S-2-amino-1,1-diphenylpropanol (7.0 g). After stirring the mixture for 20 minutes at 50° C., then 3 hours at room temperature, the precipitated crystals are collected by filtration to obtain 4.52 g. of the S-2-amino-1,1-diphenylpropanol salt of D-α-methyl-β-acetylpropionic acid; melting point: 126°–129° C.; $[\alpha]_D^{20}$: +9.0° (c=0.9, methanol). A portion of the salt is decomposed with a 3% aqueous hydrochloric acid and extracted with diethyl ether to obtain D-α-methyl-β-acetylpropionic acid in oily form; $[\alpha]_D^{20}$: −55.5° (c=1.4, chloroform).

EXAMPLE 2

To a solution of DL-α-methyl-β-acetylthiopropionic acid (5.0 g) in isopropanol (30 ml), is added with stirring at room temperature a solution of S-2-amino-1,1-diphenylpropanol (7.0 g) in isopropanol (40 ml). After 4 hours of stirring at room temperature, the precipitated crystals are collected by filtration to obtain 4.77 g of the S-2-amino-1,1-diphenylpropanol salt of D-α-methyl-β-acetylthiopropionic acid; melting point: 123°–126° C.; $[\alpha]_D^{20}$: +14.1° c=1, methanol). A portion of the salt is decomposed with a 3% aqueous hydrochloric acid and extracted with diethyl ether to obtain D-α-methyl-β-acetylthiopropionic acid in oily form; $[\alpha]_D^{20}$: −46.7° (c=1.2, chloroform).

A 3.0 g portion of the salt obtained above is recrystallized from methanol to obtain 1.4 g of the purified S-2-amino-1,1-diphenylpropanol salt of D-α-methyl-β-acetylthiopropionic acid; melting point: 130°–132° C.; $[\alpha]_D^{20}$: +8.0° (c=1, methanol). A portion of this salt is decomposed with a 3% aqueous hydrochloric acid and extracted with diethyl ether to obtain D-α-methyl-β-acetylthiopropionic acid in oily form; $[\alpha]_D^{20}$: −61.5° (c=1.2, chloroform).

EXAMPLE 3

DL-α-methyl-β-benzoylthiopropionic acid (1.12 g) and S-2-amino-1,1-diphenylpropanol (1.13 g) are dissolved in isopropanol (10 ml). After standing for 5 hours at room temperature, the precipitated crystals are collected by filtration to obtain 1.15 g of the S-2-amino-1,1-diphenylpropanol salt of L-α-methyl-β-benzoylthiopropionic acid; melting point: 130°–134° C.; $[\alpha]_D^{20}$: +42.1° (c=1, methanol). A portion of the salt is decomposed with a 3% aqueous hydrochloric acid and extracted with diethyl ether to obtain L-α-methyl-β-benzoylthiopropionic acid; melting point, 50°–53° C.; $[\alpha]_D^{20}$: +34.3° (c=1.6, chloroform).

The filtrate obtained by removing the above salt is treated in the following manner. The filtrate is concentrated to remove the isopropanol by distillation, then mixed with a 3% aqueous hydrochloric acid, and extracted with diethyl ether to obtain 0.35 g of D-α-methyl-β-benzoylthiopropionic acid; melting point, 50°–53° C.; $[\alpha]_D^{20}$: −30° (c=1, chloroform).

EXAMPLE 4

DL-α-methyl-β-benzoylthiopropionic acid (0.67 g) and S-2-amino-4-methyl-1,1-diphenylpentanol (0.81 g) are dissolved in isopropanol (4 ml) and the resulting solution is left standing overnight at room temperature. The precipitated crystals are collected by filtration to obtain 0.27 g of the S-2-amino-4-methyl-1,1-diphenylpentanol salt of L-α-methyl-β-benzoylthiopropionic acid; melting point: 90°–94° C.; $[\alpha]_D^{20}$: −5.1° (c=1, methanol).

What we claim is:

1. A process for the optical resolution of DL-α-methyl-β-acylthiopropionic acid, which comprises contacting a DL-α-methyl-β-acylthiopropionic acid of the formula,

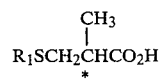

wherein $R_1$ is acetyl or benzoyl which may be substituted with a $C_1$–$C_3$ alkyl or a halogen atom, with an optically active amine of the formula,

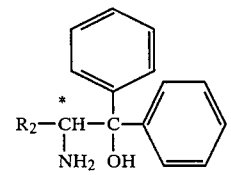

wherein $R_2$ is methyl, isopropyl or isobutyl, to form diastereoisomeric salts, subjecting the formed diastereoisomeric salts to the fractional crystallization in a solvent to separate the D-acid salt from the L-acid salt, and then contacting the individual diastereoisomeric salt with acid to give D-α-methyl-β-acylthiopropionic acid and L-α-methyl-β-acylthiopropionic acid.

2. A process according to claim 1, wherein the DL-α-methyl-β-acylthiopropionic acid and the optically active amine are used in equimolar amount.

3. A process according to claim 1, wherein the optically active amine is 2-amino-1,1-diphenylpropanol.

4. A process according to claim 1, wherein the optically active amine is 2-amino-3-methyl-1,1-diphenylbutanol.

5. A process according to claim 1, wherein the optically active amine is 2-amino-4-methyl-1,1-diphenylpentanol.

6. The process according to claim 1, wherein the optical resolution is carried out in a solvent selected from the group consisting of water, an alcohol having 1 to 4 carbon atoms and an aqueous mixture thereof.

* * * * *